United States Patent [19]

Najarian et al.

[11] 4,259,293
[45] Mar. 31, 1981

[54] FLUOROCHEMICAL VAPOR AUTOCLAVE

[75] Inventors: George L. Najarian; Zaker I. Sabri, both of Chicago, Ill.

[73] Assignee: American Dental Association Health Foundation, Chicago, Ill.

[21] Appl. No.: 98,133

[22] Filed: Nov. 28, 1979

[51] Int. Cl.³ .......................... A61L 2/06; A61L 2/20; A61L 2/24
[52] U.S. Cl. .................... 422/109; 422/113; 422/114; 422/116; 422/297; 422/299; 422/307
[58] Field of Search ................................ 422/109-114, 422/116, 31, 33, 38, 37, 300, 307, 297-299

[56] References Cited
U.S. PATENT DOCUMENTS

| | | | |
|---|---|---|---|
| 3,489,505 | 1/1970 | Schumann et al. | 422/34 |
| 3,549,312 | 12/1970 | Erust | 422/31 |
| 3,579,290 | 5/1971 | Pickstone | 422/38 |
| 3,834,872 | 9/1974 | Joslyn | 422/299 |
| 3,944,387 | 3/1976 | Schreckendgust | 422/34 |

FOREIGN PATENT DOCUMENTS 1077246  7/1967  United Kingdom .

Primary Examiner—Bradley Garris
Attorney, Agent, or Firm—Allegretti, Newitt, Witcoff & McAndrews

[57] ABSTRACT

A sterilizer utilizes fluorocarbon liquid as the sterilizing medium. The fluorocarbon liquid is retained in the bottom of a sterilizer chamber. Instruments are placed within the chamber above the liquid level. The chamber is sealed and a heater causes the liquid within the chamber to vaporize. The fluorocarbon vapor is more dense than the air within the chamber and is not miscible with that air. Consequently, as the fluorocarbon vaporizes, the air within the chamber is displaced through a vent in the top of the chamber. A minor amount of fluorocarbon vapor is also displaced as all air is purged from the chamber. The discharged fluorocarbon vapor is recondensed through an expansion valve and collected for recycling. The chamber is sealed upon purging of all the air and is maintained in a pressurized state for a period of time. Subsequently the heater is turned off and the chamber is cooled by a fan. This causes the fluorocarbon vapor to condense thereby reducing pressure within the chamber to a subatmospheric pressure. The previously discharged, condensed fluorocarbon then flows back into the chamber.

6 Claims, 1 Drawing Figure

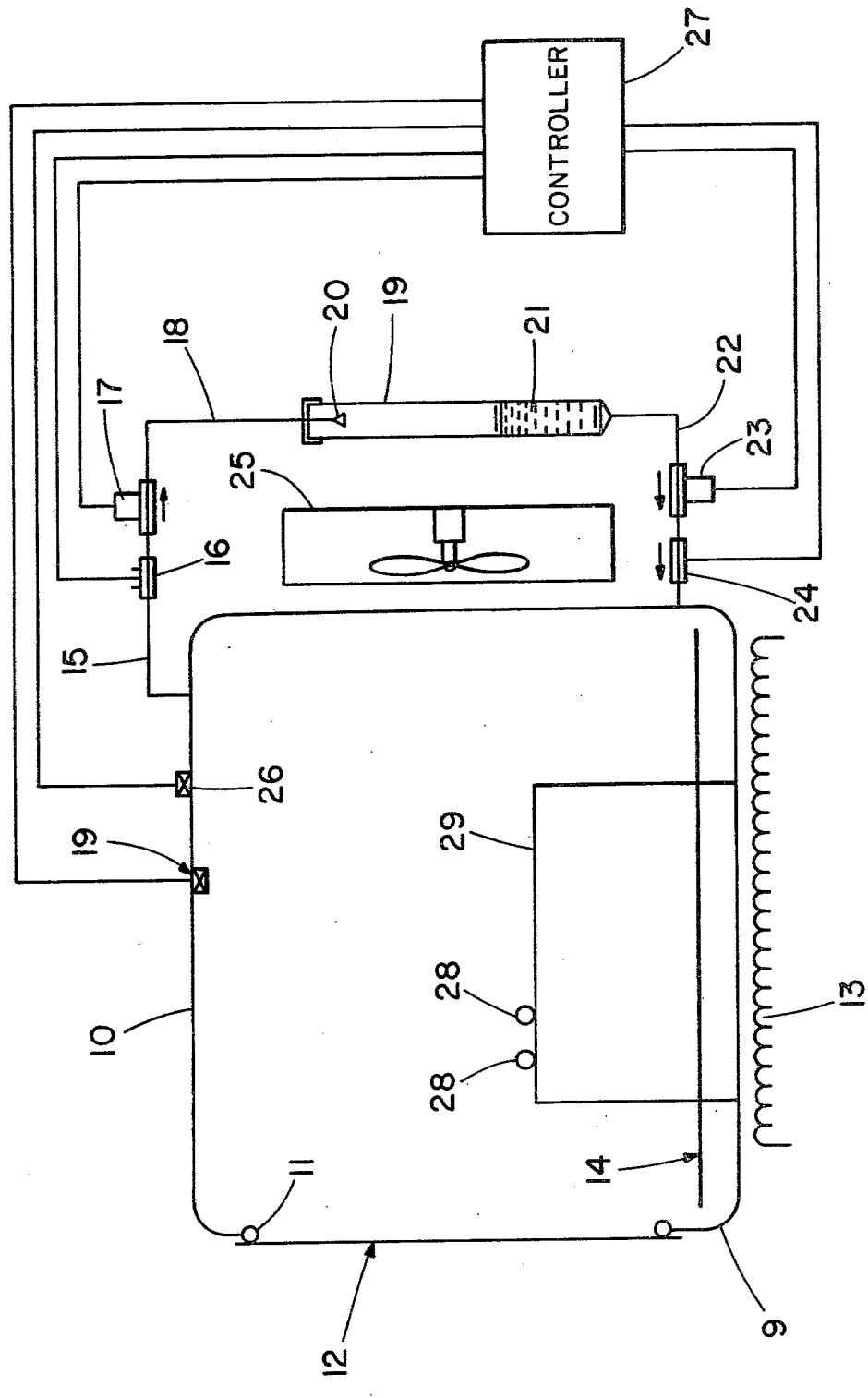

FLUOROCHEMICAL VAPOR AUTOCLAVE

BACKGROUND OF THE INVENTION

The present invention relates to an improved vapor autoclave and more particularly to a vapor autoclave which uses a fluorocarbon, that is liquid at temperatures about 100° C. and a vapor at higher temperatures.

Sterilization of surgical or dental instruments has long been considered a necessity in the medical field. Various devices have been proposed to sterilize such instruments. Among such devices are those which utilize high temperature water or steam to kill bacteria and the like. A difficulty which results with sterilization of instruments through the use of high temperature water or steam is that the steam or water becomes chemically reactive with the instruments. Consequently, the instruments are often deleteriously effected. Typical prior art steam sterilization apparatus are shown in Martin, U.S. Pat. No. 1,619,146, Christensen, U.S. Pat. No. 1,695,008 and Harvey, U.S. Pat. Nos. 2,240,001 and 2,466,234.

More recently it has been suggested that gases be introduced into a sterilizer from an external source in order to effect sterilization of surgical instruments. Schumann, et al, U.S. Pat. No. 3,489,505 teaches the cycling of ethylene oxide as the sterilizing gas in a sterilizing chamber. Schreckendgust, U.S. Pat. No. 3,944,387, teaches the introduction of a combination of ethylene oxide and a fluorocarbon into a sterilizing chamber.

Skocypec et al, U.S. Pat. No. 3,989,461, teaches another approach in the sterilization of surgical instruments. The Skocypec et al patent teaches that a liquid sterilizing material may be vaporized and then introduced into a sterilization chamber by means of a very elaborate circulation system. Pickstone, in U.S. Pat. No. 3,579,290, teaches the use of a fluorocarbon sterilizing material wherein the sterilizing fluid is retained in the chamber in a liquid form. The liquid is heated to cause a vapor. Instruments are then lowered into the vapor above the liquid to effect sterilization.

Pile, in U.S. Pat. No. 3,304,149, discloses a portable field sterilizer which is similar to the steam sterilizers previously discussed.

While the aforementioned disclosures teach sterilizer apparatus which are useful for their intended purposes, it is deemed appropriate to provide an improved sterilizer apparatus which will enhance the life of surgical instruments and will also be easy to operate and effective.

SUMMARY OF THE INVENTION

The present invention comprises an improved autoclave or sterilizer which includes a pressure chamber with a sealable access opening to the chamber. The bottom of the chamber includes a reservoir for receipt of a vaporizable fluid, such as fluorocarbon. Means are provided to support items for sterilization above the reservoir. A conduit leads from the top of the chamber for discharge of gas and vapor. The conduit connects with a vapor expansion and condensation valve mechanism which, in turn, connects with means for collecting condensed vapor and means for directing the condensed vapor back to the chamber. A control mechanism operates a heater for the fluid in the reservoir and a valving system associated with the chamber.

In operation the vaporized fluid drives less dense air from the chamber through the exit conduit. Ultimately vapor discharges through the conduit and recondenses in the condensation mechanism. After vapor is initially discharged from the conduit, a sensor actuates valving to close off the chamber. The chamber is then pressurized with a sterile vapor atmosphere. After maintaining the instruments at a fixed temperature and pressure for a period of time, the chamber is cooled and the vapor therein becomes liquified. The liquified vapor from the means for collecting is reintroduced into the reservoir. Thus, the autoclave provides a closed loop system for the vaporizable liquid which serves as the sterilizing medium.

It is, therefore, an object of the present invention to provide an improved vapor autoclave.

It is a further object of the present invention to provide an improved autoclave which comprises a closed loop system for a sterilizing medium, that medium being in a liquid form at room temperature and a vapor at sterilization temperatures.

Still a further object of the present invention is to provide an autoclave which uses a generally inert sterilant material in vapor form to sterilize various instruments and thereby eliminate degredation of the instruments.

Another object of the present invention is to provide an improved vapor autoclave having a mechanism for recovery of vapor which is expelled from the chamber of the autoclave during initial operation thereof.

One further object of the present invention is to provide an improved vapor autoclave which expells or eliminates air from the interior of the autoclave for the sterilizing operation.

These and other objects, advantages and features of the invention will be set forth in the detailed description which follows.

BRIEF DESCRIPTION OF THE DRAWING

In the detailed description which follows, reference will be made to the drawing comprising a single FIGURE which illustrates in a schematic and cross sectional view the physical arrangement of various components of the improved vapor autoclave of the present invention.

DESCRIPTION OF THE PREFERRED EMBODIMENT

Referring to the figure, the improved autoclave of the present invention is comprised of an enclosed, airtight chamber 10 which has a front access door or opening 12 with a circumferential vaportight, pressure seal 11 between the door 12 and chamber 10 so that when the door 12 is closed the chamber is sealed. A pressure of at least 20 psi may be maintained within the chamber 10.

An electric heater 13 is positioned below the bottom of the chamber 10 so that a vaporizable fluid 14 supported on the bottom of the chamber 10 can be heated and vaporized. The bottom of the chamber 10 thus serves as a fluid reservoir. The fluid 14 is preferably an inert, sterilizing liquid which is vaporizable at temperatures in excess of 100° C., which is more dense than air and which is not miscible with air. Typical fluids which satisfy these criteria are the fluorocarbons sold under the tradenames FC-75 and FC-80 by 3-M Company. These fluorocarbons have a boiling point of approximately 102° C.

A conduit 15 connects the top of the chamber 10 with a pressure sensor 16. Sensor 16, in turn, connects with a solenoid operated valve 17. The solenoid operated valve 17 connects by way of a line or conduit 18 to a dryer or condenser unit 19, and more particularly to an expansion valve 20 in combination with a molecular sieve and reservoir 21. A return conduit 22 connects from the reservoir 21 through a solenoid operated valve 23 and a check valve 24 to the interior of the chamber 10 above the level of fluid 14. A circulating fan 25 is positioned outside the chamber 10. A vapor temperature sensor 26 is positioned at the top of chamber 10.

A controller 27 controls the operation of the various valves in response to temperature and pressure readings and additionally controls the cycle time of the heater 13 by means of an internal clock mechanism. Instruments, for example surgical instruments 28, are retained on a tray or support 29 within the chamber 10 during the sterilization operation.

Thus, when operated, the door 12 is opened and instruments 28 are placed on the support rack 29 above the level of fluid 14. The door 12 is then closed and sealed. Subsequently, the controller 27 begins its operation by initially turning on heater 13. During initial heating, the valve 23, as well as the valve 17, are both closed. The liquid sterilant material, such as fluorocarbon FC-75 or FC-80, is then heated and vaporized. The hot vapors which are more dense than air and are not miscible with air rise compressing the air toward the top of the chamber 10.

Pressure within the chamber 10 is measured by the pressure sensor 16. When the vapor pressure within the chamber 10 reaches a threshold level of 16 lbs. per square inch, for example, the sensor 16 automatically sends a signal to the controller 27 which, in turn, operates the solenoid valve 17 to thereby open that valve. Air initially discharges through the conduit 15, valve 17, conduit 18 and expansion valve 20 into the dryer unit 19 where the air is permitted to escape. Finally, hot fluorocarbon vapor passes through conduit 15, valve 17, conduit 18, and expansion valve 20 into the dryer unit 19. The hot vapor passing through the expansion valve 20 is thereby cooled causing that vapor to condense into liquid form into a reservoir 21 which contains a molecular sieve. The condensation of vapor permits collection of the liquid for subsequent reintroduction into the chamber. The valve 23, however, during this part of the cycling operation, remains closed.

Ultimately the hot vapor is sensed by the vapor temperature sensor 26. At such time the temperature sensor sends a signal via controller 27 to solenoid valve 17 causing valve 17 to close. When valve 17 is closed the hot vapor entirely fills the chamber 10 as air has been substantially removed. The valve 17 remains closed for the duration of the sterilizing cycle. The term of the cycle is controlled by a timer in the controller 27. During normal operation of the sterilizing portion of the cycle, the pressure in the chamber remains at approximately 14 lbs. per square inch and 125° C. when using fluorocarbon FC-75.

After desired time for the sterilization operation, the heater 13 is turned off, solenoid valve 23 is opened and the fan 25 is turned on to accelerate cooling of the vapor. At this time check valve 24 serves to prevent vapor from escaping.

Ultimately the pressure within the chamber 10 is significantly reduced at which time the negative pressure within the chamber withdraws the collected fluid from the reservoir 21 into the chamber 10 for storage in reservoir 9.

The door 12 may then be opened and the sterilized instruments 28 removed from the chamber 10. Upon reaching an ambient temperature all valves of the system are closed and the system is ready for recycling. In this manner the fluid is continuously recycled during separate sterilizing operations.

With the structure of the present invention it is possible to reduce cycle time, retain vaporizing fluorocarbon sterilant material without the loss thereof and eliminate air contamination of the sterilizing chamber during the sterilizing operation. The structure and arrangement of the components of the present invention may be varied without departing from the scope of the invention. The invention is therefore to be limited only by the following claims and their equivalents.

What is claimed is:

1. An improved vapor autoclave comprising, in combination:

a pressure chamber with a sealable access opening, means to support items for sterilization within said chamber, and a vaporizable sterilant liquid reservoir at the bottom of the chamber;

means for heating and vaporizing a sterilant liquid;

a gas and vapor discharge conduit from the top of the chamber;

vapor expansion and condensation valve means connected with the conduit;

means for collecting condensed vapor from the valve means;

means connecting the means for collecting with the chamber; and control means for controlling the means for heating, and for controlling fluid flow through the conduit, valve means, collecting means and connecting means and providing a vapor from a vaporizable sterilant liquid in the reservoir having a vaporization temperature greater than 100° C. and a vapor form which is more dense than air and which is not miscible with air during a sterilizing cycle and providing a liquid retained within the reservoir during a nonsterilizing cycle, whereby said control means is arranged and constructed for controlling fluid flow such that the vapor from the sterilant liquid displaces air within the chamber and causes the air along with a portion of the vapor to vent through said conduit prior to initiation of the sterilizing cycle by said control means and the condensed vapor returns to the reservoir at the end of a sterilizing cycle.

2. The improved autoclave of claim 1 wherein the control means include a control for operating the means for heating to thereby vaporize a liquid; and conduit valve means for maintaining the chamber closed below a threshold pressure of vapor in the chamber and for opening the chamber upon exceeding the threshold pressure whereby vapor causes the air to be discharged through the conduit and totally vacated from the chamber.

3. The improved autoclave of claim 1 including check valve means in the conduit and connecting means to insure unidirectional flow therethrough.

4. The improved autoclave of claim 1 including vapor temperature sensing means at the top of the chamber for detecting a threshold vapor temperature.

5. The improved autoclave of claim 4 wherein said means for controlling operates to close the conduit and the connecting means upon sensing of the threshold vapor temperature so as to pressurize the chamber.

6. The improved autoclave of claim 1 wherein said means for controlling includes timing means for controlling the means for heating.

* * * * *